United States Patent
Mikulásik et al.

(10) Patent No.: US 8,883,860 B2
(45) Date of Patent: Nov. 11, 2014

(54) METHOD FOR PURIFYING DIATOMACEOUS EARTH

(75) Inventors: Endre Mikulásik, Körmend (HU); Tamás Spaits, Körmend (HU); Kálmán Nagy, Budapest (HU); Gyula Lukács, Budapest (HU); Imre Markovits, Budapest (HU); Krisztina Fodorné Kocsmár, Budapest (HU); Livia Gregorné Boros, Csömör (HU); Tamás Mórász, Budapest (HU); László Szlávik, Budapest (HU); Máté Hudák, Budapest (HU); Gyöngyi Heréb, Budapest (HU); Réka Eszter Puskás, Eger (HU); Zoltán Varga, Budapest (HU); Imre Kapui, Érd (HU); György Clementis, Siófok (HU); Gábor Attila Bacher, Budapest (HU); Beatrix Bánkövi, Budapest (HU); Gitta Kiss, Budapest (HU); Ottó Albrecht, Budapest (HU)

(73) Assignees: Egis Gyogyszergyar Nyilvanosan Mukodo Reszvenytarsasag, Budapest (HU); ONP Holdings SE, Nicosia (CY)

( * ) Notice: Subject to any disclaimer, the term of this patent is extended or adjusted under 35 U.S.C. 154(b) by 0 days.

(21) Appl. No.: 13/879,099

(22) PCT Filed: Oct. 12, 2011

(86) PCT No.: PCT/HU2011/000098
§ 371 (c)(1),
(2), (4) Date: May 14, 2013

(87) PCT Pub. No.: WO2012/049527
PCT Pub. Date: Apr. 19, 2012

(65) Prior Publication Data
US 2013/0225695 A1     Aug. 29, 2013

(30) Foreign Application Priority Data
Oct. 12, 2010 (HU) .................................... 1000547

(51) Int. Cl.
*A61K 47/02* (2006.01)
(52) U.S. Cl.
USPC ........................................................ 514/770

(58) Field of Classification Search
USPC .......................................................... 514/770
IPC ...................... C01B 33/143,33/12; A61K 47/02
See application file for complete search history.

(56) References Cited

U.S. PATENT DOCUMENTS

| 5,656,568 | A | 8/1997 | Shiuh et al. |
| 6,653,255 | B2 | 11/2003 | Shiuh et al. |
| 2001/0023233 | A1 | 9/2001 | Shiuh et al. |
| 2013/0149380 | A1* | 6/2013 | Mikulasik et al. ............ 424/474 |

FOREIGN PATENT DOCUMENTS

| CN | 1618734 A | 5/2005 |
| CN | 1883739 A | 12/2006 |
| EP | 0758560 A1 | 2/1997 |
| GB | 1299798 A | 12/1972 |
| HU | 2011 000272 | * 1/2012 |

OTHER PUBLICATIONS

San O. et al. Purification of Diatomite Powder by Acid Leaching for Use in Fabrication of Porous Ceramics. International J of Mineral Processing 93(1)6-10, Sep. 1, 2009.*
International Search Report for PCT/HU2011/000098 (Jun. 8, 2012).
International Preliminary Report on Patentability for PCT/HU2011/000098 (Apr. 16, 2013).
Abstract for JP 11-000554 A (Jan. 6, 1999).
Database WPI Week 200739, Thomson Scientific, London, GB; AN 2007-404423—XP-002677359.
Database WPI Week 200568, Thomson Scientific, London, GB; AN 2005-659522—XP-002677360.
R. Goren et al., "A Study on the Purification of Diatomite in Hydrochloric Acid", Scandinavian Journal of Metallurgy, vol. 31, No. 2 (Apr. 2002) pp. 115-119.
O. San et al., "Purification of Diatomite Powder by Acid Leaching for use in Fabrication of Porous Ceramics", International Journal of Mineral Processing, vol. 93, No. 1 (Sep. 1, 2009) pp. 6-10.

* cited by examiner

*Primary Examiner* — Ralph Gitomer
(74) *Attorney, Agent, or Firm* — Millen, White, Zelano & Branigan, P.C.

(57) ABSTRACT

A method for purifying diatomaceous earth, whose natural colloidal structure is retained, which includes preparing a suspension of diatomaceous earth in a liquid wherein diatomaceous earth is insoluble, separating diatomaceous earth from the suspension, treating diatomaceous earth with an inorganic or organic acid, heat-treating the thus obtained product at a temperature not higher than 300° C., subjecting the product obtained to oxidative treatment and drying the purified product.

25 Claims, No Drawings

METHOD FOR PURIFYING DIATOMACEOUS EARTH

TECHNICAL FIELD OF THE INVENTION

The present invention is related to a method for preparation of a pharmaceutical excipient, more specifically the purification of diatomaceous earth suitable for use in the pharmaceutical industry. The principle of the present invention resides in that during the purification method according to the present invention, only such steps are employed wherein the natural colloidal structure of diatomaceous earth remains unchanged.

BACKGROUND ART

Diatomaceous earth (siliceous earth, diatomite) is a mineral mainly comprising of amorphous silicone dioxide having a natural colloidal structure and high specific surface area originating from the fossil frustules (the hard and porous cell wall or external layer) of diatomaceous algae (Diatoms). Besides the frustules of diatomaceous algae, diatomaceous earth contains further minerals in various amounts (e.g. montmorillonite, caolinite, quartz, feldspar, calcite). Diatomaceous earth is a loamy, earthy, soft, easily dispersible, fine-grained, usually light-coloured silicon-containing sedimentary mineral. It is of natural origin formed from the bulk deposition of the frustules of fossil Diatoms in salty and freshwater lakes and seas of the early Jurassic period. Many occurances of the diatomaceous earth are known worldwide.

Diatomaceous earth is used in various fields of the industry. It has been used for a long time in the chemical, cosmetical and pharmaceutical industry as a general auxiliary agent having high sorption capacity and relative lack of chemical reactivity.

During the use in the chemical industry, high specific surface area of diatomaceous earth particles is exploited. Although specific surface area of artificial amorphous silicone dioxide derivatives (e.g. Aerosil) is similarly high, diatomaceous earth exhibit far more advantageous properties during pharmaceutical formulation methods involving compression than said artificial silicaceous products. Diatomaceous earth has favourable pore structure comprising macro- meso- and micropores, which provides advantageous wetting and adsorption properties during the formulation of hydrophilic and hydrophobic materials or mixtures including emulsions or colloidal systems.

Since diatomaceous earth is a naturally occuring material of organic origin, a critical characteristic of the product is its purity. Diatomaceous earth is produced by mining the natural deposit, separating, calcining and chemically purifying the mineral. (Lloyd de Antonides 1998, Diatomite U.S. Geological Survey Mineral Commodity Summaries 1998; Tasnády Kubacska András: Ásványok).

A common feature of silicon-containing preparations used in the pharmaceutical industry is that these materials are purified by calcination. Calcined diatomaceous earth has been admitted into the United States Pharmacopoeia. The principle of the manufacturing method disclosed in the pharmacopoeial monograph resides in separating crude diatomaceous earth in an air jet mill or by sieving, separating silicon-containing part from carbonates by acidic treatment and heat-treating (calcining) the resulting material at a high temperature (calcination at 900-1100° C.). During the heat treatment, volatile impurities are vaporized and thereby removed and the solid material partially melts, thus forming beads. The treated material is milled and the acidic treatment is optionally repeated in order to remove acid-soluble components. The diatomaceous earth powder is dried and sized. While this method yields a product having adequate chemical purity, the natural structure of diatomaceous earth originating from diatomaceous algae is broken, thus destroying the greater part of macro- and mesoporous structure.

There are no known purification methods in the prior art which are devoid of calcination step. For example, in published U.S. Pat. No. 2,164,500, the calcining step is essential. Published U.S. Pat. No. 4,325,844 discloses an energy-efficient method for calcination, which involves the treatment of diatomaceous earth at a temperature which is significantly higher than that applied in method of the present invention.

Chinese Patent Application No. 100346858 is related to a method for purification of diatomaceous earth and a process for removing lubricant oil therefrom, which comprises wetting of diatomaceous earth, treating the wetted solid with an acid, preferably using sulfuric acid and filtering, neutralizing and dehydrating the solids.

Chinese Patent Application No. 1401567 is related to purification of diatomaceous earth by acidic treatment using oxalate or phosphate, thereafter thoroughly stirring, ultrasonically treating or boiling the mixture. Subsequently the solids are allowed to settle and the iron-containing sediment is removed magnetically.

Chinese Patent Application No. 1322673 is related to a two-step method for the purification of diatomaceous earth. In the first step, the structure of the inorganic impurities is transformed by heat-treatment. Subsequently in the second step, the material is treated with sulfuric acid while heating at low temperature until a purified silicone dioxide product is obtained.

Published Japanese Patent Application No. 2001097711 discloses a method for purification of diatomaceous earth free of boron impurity and suitable for manufacturing silicone semiconductors, which comprises the steps of acidic treatment optionally followed by neutralization with a basic reagent; heating and separating diatomaceous earth at a suitable pH and optionally treating diatomaceous earth with a suitable salt, for example, aluminium nitrate.

SUMMARY OF THE INVENTION

The disadvantage of the methods according to the prior art resides in that these methods involve one or more steps which damage or destroy the natural physical structure of diatomaceous earth, which results in a chemically purified product having different structure from that of the natural structure of diatomaceous earth. Such products lack the superior compressibility properties of diatomaceous earth having the natural structure. At the same time, however, providing diatomaceous earth in suitable chemical purity is essential since impurities present therein can interact with the active ingredient of the formulation and such interactions may affect bioavaibility or stability of the active ingredient.

The objective of the present invention is providing a new method for preparing diatomaceous earth in a chemically purified form wherein the valuable natural structure of raw diatomaceous earth is retained since the original boat-, cylinder-, comb-, box-like structures of the outer wall or layer (frustules) of Diatom algae with micro- meso- and macroporous structure are preserved essentially unchanged. Obtaining a diatomaceous earth product with the structure of natural diatomaceous earth provides for the exploitation of advantages thereof in the pharmaceutical technology.

The principle of the present invention resides in that during the purification method according to the present invention, only such steps are employed wherein the natural colloidal structure of diatomaceous earth remains unchanged.

The method according to the present invention comprises exclusively simple physical or chemical steps (acidic or oxidative treatment, separation, drying) thus preserving the natural structure of diatomaceous earth. At the same time, it was surprisedly observed that the chemical purity of the product obtained by the method according to the present invention is better than that of the products obtained according to the methods known from the prior art.

DETAILED DESCRIPTION OF THE INVENTION

According to the first aspect of the present invention, there is provided a method for preparation of diatomaceous earth suitable for use in the pharmaceutical industry, wherein the natural structure of diatomaceous earth is retained, which comprises providing a suspension of raw diatomaceous earth in a liquid wherein diatomaceous earth is not soluble; separating diatomaceous earth from said suspension optionally by applying ultrasonic irradiation; treating the separated diatomaceous earth with an organic or inorganic acid optionally by applying simultaneous ultrasonic irradiation; heating the thus obtained diatomaceous earth at a temperature not higher than 300° C.; purifying the heat-treated diatomaceous earth by oxidative treatment optionally applying simultaneous ultrasonic irradiation and drying the purified diatomaceous earth product.

According to the present invention, in the first step of the purification method, any polar or apolar organic solvents which are not dissolving the diatomaceous earth can be used for the preparation of the suspension. Preferably water is used.

Separation in the second step is preferably carried out by sieving using a suitable mesh size. Suitable mesh sizes are 0.5 mm or smaller which are suitable for retaining particles of impurities and accompanying materials to diatomaceous earth, e.g. calcite. Preferably, a sieve having 0.25 mm or smaller mesh size is used. If desired, ultrasonic irradiation can be applied during the processing of diatomaceous earth having a predetermined radiation profile and radiation power. The frequency range suitable for ultrasonic treatment (sonication) is between 16 and 42 kHz while the continous or pulse ultrasonic power is 0.1 to 10 kW. The most advantageous frequency range is between 20 and 42 kHz with 0.5 to 2 kW ultrasonic power.

In the third step of the purification process comprising an acidic treatment of the separated diatomaceous earth, an inorganic or an organic acid is used. Preferable acids for such treatment include but are not limited to the inorganic acids such as hydrochloric acid, sulfuric acid, sulfurous acid, nitric acid, nitrous acid, phosphorous-containing acids such as hypophosphorous acid, phosphoric acid, hypophosphoric acid, ortophosphoric acid, pyrophosphoric acid, metaphosphoric acid, boron-containing acids, e.g. ortoboric acid, metaboric acid, pyroboric acid, chlorine-containing oxo-acids such as hypochlorous acid, hypochloric acid, chlorous acid, chloric acid, perchloric acid, bromine-containing oxoacids, e.g. hypobromous acid, hypobromic acid, bromous acid, bromic acid, perbromic acid; less concentrated hydrogen fluoride and the like. Suitable organic acids include but are not limited to acetic acid, citric acid, formic acid, carbonic acid, butyric acid, phtalic acid, tartaric acid and the like. Inorganic mineral acids, such as hydrochloric acid, nitric acid and sulfuric acid are preferred.

In most cases, the acid can be used as concentrated acid or an aqueous solution thereof. When hydrochloric acid is used, the method is most efficient if hydrochloric acid solution having 6 to 12 weight % concentration, preferably concentrated hydrochloric acid solution diluted at least with threefold volume of water is used. Water is preferred for the dilution of an acid, but any polar or apolar liquid can be used wherein the solubility of diatomaceous earth is less than 500 g/dm$^3$ and which is miscible with the acid.

During the acidic treatment, acid-soluble impurities of diatomaceous earth are dissolved. The temperature of the acidic treatment is between the melting point and the boiling point of the acid or the diluted solution of the acid at atmospheric pressure. Preferably, the temperature of the acidic treatment is close the boiling point of the acidic reagent. It is especially advantageous to carry out the acidic treatment at the boiling point of the acidic reagent mixture. If desired, ultrasonic irradiation having a predetermined radiation profile and radiation power can be applied during the acidic treatment. The frequency range suitable for ultrasonic treatment is between 16 and 42 kHz while the continous or pulse ultrasonic power is 0.1 to 10 kW. The most advantageous frequency range is between 20 and 42 kHz with 0.5 to 2 kW ultrasonic power.

The efficiency of the treatment can be improved by using oxidizing reagents, e.g. hydrogen peroxide simultaneously. However, any oxidizing agent mentioned below in connection with the oxidation step of the method can be used in this phase of purification as well.

In the fourth step of the process, diatomaceous earth subjected to acidic treatment is heat-treated in a furnace. The temperature of heat treatment according to the present invention is 300° C. or lower, preferably 250±25° C. The duration of the heat treatment is between 10 minutes and 24 hours, preferably 6 hours.

In the fifth step, the heat-treated product is subjected to further purification by an oxidative treatment. During this step, the heat-treated diatomaceous earth is stirred in a solution of an oxidizing agent having appropriate pH at a predetermined temperature for a sufficient period, optionally simultaneously subjecting the suspension of diatomaceous earth and oxidizing agent to ultrasonic irradiation.

The scope of oxidizing agents is not limited to any particular reagent. Inorganic or organic oxidizing reagents can be used. Particularly suitable oxidizing agents are hydrogen peroxide, organic peroxides (e.g. peroxodisulfuric acid, peroxosulfuric acid), permanganic acid ($HMnO_4$) and salts thereof (e.g. potassium permanganate, $KMnO_4$) dichromic acid ($H_2Cr_2O_7$) and salts thereof (e.g. potassium dichromate, $K_2Cr_2O_7$), chromic acid or salts thereof, aqueous chlorine solution, mixtures of hydrochloric acid and hydrogen peroxide, mixture of aqueous ammonia solution and hydrogen peroxide, oxidizing gases (e.g. oxygen, ozone, fluorine, chlorine, bromine). Particularly advantageous oxidants are hydrogen peroxide, peroxosulfuric acid and peroxodisulfuric acid or solutions thereof.

According to the method of the present invention, the oxidizing agent can be used in the form of a saturated or a diluted solution. Practically, a solution of the oxidizing reagent having 0 to 50 weight % concentration is used. Preferably, the concentration of the oxidizing reagent can be set to 0.05 to 50, preferably 1 to 40 weight %. During the oxidative treatment, the pH of the liquid phase has to be selected according to the oxidizing agent. In the case when hydrogen peroxide solution is used, alkaline pH is especially advantageous.

The temperature of the oxidative treatment is depending on the quality of the oxidizing agent. For example, in case of hydrogen peroxide, room temperature is preferable. The duration of the oxidative treatment is at least 1 minute, however, it is advantageous to contact the diatomaceous earth with the oxidating reagent for a longer period. Suitable period of oxidative treatment is approx. 25 minutes but depending on the composition of the diatomaceous earth to be purified and the oxidizing reactant, the duration of the treatment can be increased up to 1-3 days.

If desired, during the oxidative treatment, ultrasonic irradiation having a predetermined radiation profile and radiation power can be applied. The frequency range suitable for ultrasonic treatment is between 16 and 42 kHz while the continous or pulse ultrasonic power is 0.1 to 10 kW. The most advantageous frequency range is between 20 and 42 kHz with 0.5 to 2 kW ultrasonic power.

The product obtained from the oxidative treatment is subsequently dried. The drying operation is carried out in a drying cabinet or in a fluid-bed dryer at atmosperic pressure or in vacuo. During the drying, the wet product is treated for a predetermined period of time at a predetermined temperature and pressure optionally using a drying fluid.

The minimum drying temperature is 50° C. It is advantageous to carry out the drying process at a temperature close to the boiling point of the solvent used in the oxidizing step. In most cases, it is especially preferable to perform the drying process at 90° C.

The drying can be carried out at the atmospheric pressure or in vacuo. Preferable pressure for drying is less than 15 kPa. Using vacuum is advantageous, especially preferable to carry out the drying at the pressure of 20±10 torr.

The length of the drying period is at least 1 hour but depending on the drying temperature and the solvent to be dried, it can be increased up to several days. Drying is carried out preferably for 20±0.5 hours.

When drying is carried out by applying a drying fluid, the process is carried out in a fluid-bed dryer. Advantageous drying fluids are inert gases, e.g. air, nitrogen, noble gases etc.

By carrying out the method according to the present invention, a diatomaceous earth product can be obtained wherein the natural colloidal structure of diatomaceous earth is retained and which has suitable purity for the use in the pharmaceutical industry. The retention of said natural colloidal structure can be assessed by imaging or surface analytical methods including but not limited to optical or electronmicroscopy.

The quality of diatomaceous earth produced according to the present invention can be tested and controlled using methods known in the art. As an example, methods of the corresponding pharmacopoeial monographs can be used. Silicon dioxide content can be determined on the basis of the loss of weight upon reacting diatomaceous earth with hydrogen fluoride. Metal impurities, such as arsenic and especially heavy metals cadmium, lead and mercury can be assayed by atomic absorption spectroscopy (AAS) or by X-ray fluorescence spectroscopy (XRF). As a guidance, an XRF assay disclosed in EPA6200 method is suitable for the assay of metal impurities. Amorphous or crystalline phases can be studied by X-ray diffraction analysis.

The method according to the present invention is demonstrated by the following examples without limiting said method to the examples only.

EXAMPLES

Example 1

Analysis Results of the Impurities in Commercially Available Diatomaceous Earth Preparation and in Diatomaceous Earth Purified According to the Present Invention Table 1 exhibits the most important impurities of diatomaceous earth. In Table 1, the concentrations of the individual impurities (expressed in weight %) are compared for the diatomaceous earth purified according to the method of the present invention and commercially available diatomaceous earth purified by calcination. Assays were carried out by X-ray fluorescence analysis (XRF) using a Spectro Xepos energy-dispersive X-ray fluorescence spectrometer.

Measurements were carried out using approx. 3 g sample, a 32-mm sample vial and using ProleneFilm. During the measurements, He flushing was applied. The following three targets were used:

| Target: | Energy | Measurement time |
|---|---|---|
| 1., Mo | 25 keV | 300 s |
| 2., Al$_2$O$_3$ | 50 keV | 300 s |
| 3. Bragg crystal, HOPG | 12.5 keV range | 300 s |

During the measurements, samples are irradiated by X-ray radiation and analysis was carried out by an energy-dispersive measurement method. Calibration is carried out empirically using normalization method.

TABLE 1

| | Na | Mg | Al | S | Ca | Fe | P | K | Ti |
|---|---|---|---|---|---|---|---|---|---|
| Diatomaceous earth purified according to the invention | 0.112 | 0 | 0.373 | 0.023 | 0.154 | 0.080 | 0.019 | 0.068 | 0.030 |
| Celpure C1000 | 0.249 | 0 | 1.817 | 0.022 | 0.166 | 0.713 | 0.021 | 0.026 | 0.091 |
| Celpure C300 | 0.157 | 0.042 | 0.509 | 0.028 | 0.096 | 0.846 | 0.036 | 0.097 | 0.080 |
| Celite 535 NF | 0.162 | 0.191 | 1.702 | 0.027 | 0.375 | 1.427 | 0.055 | 0.322 | 0.145 |
| Celite 545 NF | 0.154 | 0.187 | 1.622 | 0.020 | 0.372 | 1.432 | 0.049 | 0.319 | 0.145 |
| Celite Hyflo | 0.301 | 0.170 | 1.608 | 0.028 | 0.430 | 1.645 | 0.047 | 0.409 | 0.192 |

From the data of Table 1 it is apparent that diatomaceous earth purified according to the method of the present invention has higher purity (i.e. the concentration of the particular impurity is lower) with regard to almost all impurities listed in Table 1 than that in case of commercially available diatomaceous earth preparations. Consequently, it can be concluded that according to the method of the present invention, the diatomaceous earth excipient having high degree of purity exceeding that of the commercially available similar products can be produced while retaining the natural colloidal structure of diatomaceous fustules.

Example 2

1. Suspending and Separating

Wet raw diatomaceous earth was dispersed in a reaction vessel using 7.5 kg of water and was subsequently sieved using a 0.25-mm mesh sieve.

The purity of the product was analyzed by XRF. According to the measurements, the product contained 35 weight % Si, 8 weight % Ca. Loss of ignition, 16%. Assay (expressed as silicon dioxide, $SiO_2$): 68 weight %.

2. Acidic Treatment

The sieved fraction wherein the size of the suspended particles is smaller than 0.25 mm, obtained in 1 is used.

Into the suspension, 2.875 kg (2.5 l) concentrated hydrochloric acid are added in 15±5 minutes while removing the evolved hydrogen sulfide containing gases by suction. After the evolution of gases subsided, the suspension is stirred at 25° C. for 30 minutes. The mixture is heated until reflux temperature and kept under reflux for 24 hours. Subsequently the suspension is filtered while hot, suspended in the vessel with 7.5 kg hot water and filtered while hot. The last suspending step is repeated five times with the same amount of hot water.

The product was analyzed by XRF. Analysis: Si 50 weight %, Ca 0.1 weight %. Loss of ignition: 9 weight %. Assay (expressed as silicone dioxide, $SiO_2$): 99 weight %.

3. Heat Treatment

The wet material is subjected to heat treatment for 6.5±0.5 hours at 250° C. in a furnace. The heat-treated product is subjected to XRF analysis. Analysis: Si 54 weight %, Ca 0.1 weight %. Loss of ignition, 3 weight %. Assay (expressed as silicone dioxide, $SiO_2$), 99 weight %.

4. Oxidative Treatment

The heat-treated product is transferred into a vessel and 8.325 kg (7.5 l) of 35% hydrogen peroxide solution and 0.5 kg of 10 weight % sodium hydroxide solution are added. The mixture is treated by sonication for 25 minutes using an ultrasonic probe while care is exercised to prevent foaming. Subsequently the suspension is filtered and the product is washed with 1.25 kg of water.

5. Drying

The product was dried in a drying cabinet at the temperature of 90° C. spread out in a thin layer for 20±0.5 hours, allowed to cool at atmospheric pressure and packaged.

The product is analyzed by XRF. Analysis: Si, 53 weight %; Ca, 0.1 weight %. Loss of ignition, 3 weight %. Assay (expressed as silicone dioxide, $SiO_2$): 99 weight %.

What we claimed is:

1. A method for purifying diatomaceous earth wherein the natural colloidal structure of the diatomaceous earth material is retained, which comprises the following steps
    preparing a suspension of raw diatomaceous earth in a liquid in which diatomaceous earth is insoluble,
    separating the diatomaceous earth from the suspension,
    treating the diatomaceous earth with an inorganic or organic acid,
    heat-treating the thus obtained product at a temperature not higher than 300° C.,
    subjecting the product obtained to oxidative treatment and drying the purified product.

2. A method according to claim 1, wherein simultaneously to any of the steps, ultrasonic irradiation is applied.

3. A method according to claim 1, wherein the liquid for preparing the suspension is water.

4. A method according to claim 1, wherein the diatomaceous earth is separated from the suspension by sieving.

5. A method according to claim 4, wherein the sieving is carried out by a using a sieve with a mesh size of 0.5 mm or smaller.

6. A method according to claim 1, wherein during the separating of the diatomaceous earth from the suspension ultrasonic irradiation is applied.

7. A method according to claim 1, wherein the inorganic or organic acid is a mineral acid.

8. A method according to claim 1, wherein the treating of the diatomaceous earth with an inorganic or organic acid is performed in the presence of water as a diluent.

9. A method according to claim 1, wherein the treating of the diatomaceous earth with an inorganic or organic acid is performed by an acidic solution having a concentration of 6 to 12 weight %.

10. A method according to claim 1, wherein the treating of the diatomaceous earth with an inorganic or organic acid is performed in the additional presence of an oxidizing reagent.

11. A method according to claim 1, wherein simultaneously to the treating of the diatomaceous earth with an inorganic or organic acid ultrasonic irradiation is applied.

12. A method according to claim 1, wherein the heat-treating of the thus obtained product is at a temperature lower than 300° C.

13. A method according to claim 1, wherein the heat-treating of the thus obtained product is at a temperature of 250±25° C.

14. A method according to claim 1, wherein the heat-treating of the thus obtained product is for a period between 10 minutes and 24 hours.

15. A method according to claim 1, wherein the subjecting of the product obtained to oxidative treatment is performed by an organic oxidizing agent.

16. A method according to claim 1, wherein the subjecting of the product obtained to oxidative treatment is performed in a liquid phase containing an oxidizing agent, the pH of which liquid phase is selected according to the oxidizing agent.

17. A method according to claim 1, wherein the subjecting of the product obtained to oxidative treatment is performed by 0-50 weight % hydrogen peroxide solution.

18. A method according to claim 1, wherein the subjecting of the product obtained to oxidative treatment is for a duration of between 1 minute and 3 days.

19. A method according to claim 1, wherein simultaneously to the subjecting of the product obtained to oxidative treatment ultrasonic irradiation is applied.

20. A method according to claim 1, wherein the drying of the purified product is carried out at a temperature between 50 and 90° C.

21. A method according to claim 1, wherein the drying of the purified product is carried out at atmospheric pressure or in vacuo.

22. A method according to claim 1, wherein the drying of the purified product is carried out at 20±10 Torr pressure.

23. A method according to claim 1, wherein the drying of the purified product is for a duration of between 1 hour and 3 days.

24. A method according to claim 2, wherein the ultrasonic treatment has a frequency and power of between 16 and 42 kHz and between 0.1 and 10 kW.

25. A method according to claim 1, wherein the subjecting of the product obtained to oxidative treatment is performed by an inorganic oxidizing agent.

* * * * *